(12) United States Patent
Sutermeister et al.

(10) Patent No.: US 12,042,219 B2
(45) Date of Patent: *Jul. 23, 2024

(54) ELECTROPHYSIOLOGY DEVICE WITH ELECTRODES HAVING INCREASED SURFACE AREA

(71) Applicant: St. Jude Medical, Cardiology Division, Inc., St. Paul, MN (US)

(72) Inventors: Derek Sutermeister, Ham Lake, MN (US); Edward E. Parsonage, St. Paul, MN (US); Gregory K. Olson, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/069,370

(22) Filed: Dec. 21, 2022

(65) Prior Publication Data

US 2023/0240744 A1 Aug. 3, 2023

Related U.S. Application Data

(63) Continuation of application No. 16/193,610, filed on Nov. 16, 2018, now Pat. No. 11,559,350.

(Continued)

(51) Int. Cl.
*A61B 18/14* (2006.01)
*B23K 26/352* (2014.01)
(Continued)

(52) U.S. Cl.
CPC ........ *A61B 18/1492* (2013.01); *B23K 26/355* (2018.08); *C25D 7/00* (2013.01);
(Continued)

(58) Field of Classification Search
CPC ...... A61B 18/1492; A61B 2017/00526; A61B 2018/00011; A61B 2018/00119;
(Continued)

(56) References Cited

U.S. PATENT DOCUMENTS 5,239,999 A  8/1993  Imran
5,632,770 A * 5/1997  Schaldach ............. A61B 5/283
                                                         607/129

(Continued)

FOREIGN PATENT DOCUMENTS

WO     96/32897     10/1996
WO    2006/121883   11/2006
(Continued)

OTHER PUBLICATIONS

International Search Report and Written Opinion for PCT/US2016/031105, dated Jul. 26, 2016.

(Continued)

*Primary Examiner* — Linda C Dvorak
*Assistant Examiner* — Lindsay Regan Lancaster
(74) *Attorney, Agent, or Firm* — Wiley Rein LLP

(57) ABSTRACT

A medical device includes a body and at least one electrode disposed thereon. The electrode includes a metallic substrate, such as a platinum group metal, an alloy of platinum group metals, or gold. The surface of the substrate is modified in a manner that increases its effective surface area without inducing bulk heating. For example, the surface of the substrate can be laser textured and/or coated, such as with titanium nitride or iridium oxide.

21 Claims, 5 Drawing Sheets

Related U.S. Application Data

(60) Provisional application No. 62/591,656, filed on Nov. 28, 2017.

(51) Int. Cl.
  *C25D 7/00* (2006.01)
  *A61B 17/00* (2006.01)
  *A61B 18/00* (2006.01)
  *A61N 1/04* (2006.01)
  *A61N 1/05* (2006.01)
  *A61N 1/362* (2006.01)
  *C23C 14/02* (2006.01)
  *C23C 16/02* (2006.01)
  *C25D 5/34* (2006.01)

(52) U.S. Cl.
  CPC ........ *A61B 2017/00526* (2013.01); *A61B 2018/00011* (2013.01); *A61B 2018/00119* (2013.01); *A61B 2018/00136* (2013.01); *A61B 2018/00148* (2013.01); *A61B 2018/00178* (2013.01); *A61B 2018/00351* (2013.01); *A61B 2018/00577* (2013.01); *A61B 2018/00642* (2013.01); *A61B 2018/00839* (2013.01); *A61B 2018/1467* (2013.01); *A61N 1/0472* (2013.01); *A61N 1/05* (2013.01); *A61N 1/362* (2013.01); *C23C 14/022* (2013.01); *C23C 16/0227* (2013.01); *C25D 5/34* (2013.01)

(58) Field of Classification Search
  CPC ........ A61B 2018/00136; A61B 2018/00148; A61B 2018/00178; A61B 2018/00351; A61B 2018/00577; A61B 2018/00642; A61B 2018/00839; A61B 2018/1467; B23K 26/355; C25D 7/00; C25D 5/34; A61N 1/0472; A61N 1/05; A61N 1/362; C23C 14/022; C23C 16/0227
  See application file for complete search history.

(56) References Cited

U.S. PATENT DOCUMENTS

| | | |
|---|---|---|
| 7,676,274 B2 | 3/2010 | Hung et al. |
| 8,560,086 B2 | 10/2013 | Just et al. |
| 9,289,594 B2 | 3/2016 | Petersen et al. |
| 11,559,350 B2 * | 1/2023 | Sutermeister ............ C25D 7/00 |
| 2004/0220652 A1 * | 11/2004 | Zhou .................... C25D 5/623 607/141 |
| 2008/0281391 A1 | 11/2008 | MacAdam et al. |
| 2009/0099634 A1 * | 4/2009 | Atanasoska .......... A61N 1/0565 607/121 |
| 2009/0118818 A1 * | 5/2009 | Foss ........................ A61L 31/14 623/1.42 |
| 2017/0112405 A1 | 4/2017 | Sterrett et al. |

FOREIGN PATENT DOCUMENTS

| | | |
|---|---|---|
| WO | 2016/182876 | 11/2016 |
| WO | 2019/036653 | 2/2019 |

OTHER PUBLICATIONS

Doroszkowski, A., "Paint and Surface Coatings", The Physical Chemistry of Dispersion, 1999.
Nave, R., "Resistivity and Conductivity", Apr. 9, 2000.

* cited by examiner

ELECTROPHYSIOLOGY DEVICE WITH ELECTRODES HAVING INCREASED SURFACE AREA

CROSS-REFERENCE TO RELATED APPLICATIONS

This application is a continuation of U.S. application Ser. No. 16/193,610, filed 16 Nov. 2018 ("the '610 application"), now U.S. Pat. No. 11,559,350, which claims the benefit of U.S. provisional application No. 62/591,656, filed 28 Nov. 2017 ("the '656 provisional"). The '610 application and the '656 provisional are hereby incorporated by reference as though fully set forth herein.

BACKGROUND

The instant disclosure relates to catheters for use in medical procedures, such as electrophysiology studies. In particular, the instant disclosure relates to electrophysiology catheters that include electrodes with increased surface area and decreased impedance.

Catheters are used for an ever-growing number of procedures, such as diagnostic, therapeutic, and ablative procedures, to name just a few examples. Typically, the catheter is manipulated through the patient's vasculature and to the intended site, for example, a site within the patient's heart.

A typical electrophysiology catheter includes an elongate shaft and one or more electrodes on the distal end of the shaft. The electrodes may be used for ablation, diagnosis, or the like. Oftentimes, these electrodes include ring electrodes that extend about the entire circumference of the catheter shaft, as well as a tip electrode.

As the dimensions of a measurement electrode decrease, the complex AC impedance with respect to a counter-electrode will generally increase. The increased impedance associated with smaller measurement electrodes can have undesirable effects during electrophysiology studies, such as electroanatomical mapping.

There are two primary contributing factors to the increased impedance. A first contributing factor is related to the dimensional dependence of the volumetric resistance (i.e., smaller electrodes have regions of higher current density). A second contributing factor is related to the capacitance of the electrode (i.e., as electrode dimensions shrink, the ionic AC current can become limited by how much charge can build up at the electrode surface). The second contributing factor, therefore, depends upon the total microscopic surface area of the electrode versus the macroscopic dimensional surface area of the electrode.

BRIEF SUMMARY

Disclosed herein is a method of manufacturing a medical device, including: forming a medical device body; forming at least one electrode according to a process including: forming a metallic substrate; and treating a surface of the metallic substrate in a manner that increases an area of the surface of the metallic substrate and that reduces the real component of impedance (resistance) of the metallic substrate when operating at a frequency within a cardiac medical range (e.g., less than about 20 kHz); and securing the at least one electrode to the medical device body. The metallic substrate can be selected from the group consisting of gold, platinum group metals (e.g., ruthenium, rhodium, palladium, osmium, iridium, and platinum), and alloys of platinum group metals (e.g., platinum-iridium alloy).

In aspects of the disclosure, the surface of the metallic substrate is treated by applying laser energy to the surface of the metallic substrate, for example using a femtosecond laser, thereby texturing the surface of the metallic substrate. In other aspects of the disclosure, the surface of the metallic substrate can be treated by applying a coating, such as titanium nitride, iridium oxide, platinum, platinum iridium, and/or an electro-conductive polymer coating thereto. The coating may be applied by chemical vapor deposition, physical vapor deposition, or electrochemical deposition. In still other aspects of the disclosure, the surface of the metallic substrate is both laser-textured and coated, with the treatments occurring in either order.

Also disclosed herein is a medical device, such as a multi-electrode electrophysiology catheter, formed according to a process, including the steps of: forming a medical device body; forming at least one electrode according to a process including: forming a metallic substrate; and treating a surface of the metallic substrate in a manner that increases an area of the surface of the metallic substrate and that reduces the resistance of the metallic substrate when operating at a frequency within a cardiac medical range (e.g., less than about 20 kHz); and securing the at least one electrode to the medical device body. The coating may be applied by chemical vapor deposition, physical vapor deposition, or electrochemical deposition. The metallic substrate can be selected from the group consisting of gold, platinum group metals, and alloys of platinum group metals.

In aspects of the disclosure, the surface of the metallic substrate is treated by applying laser energy to the surface of the metallic substrate, for example using a femtosecond laser, thereby texturing the surface of the metallic substrate. In other aspects of the disclosure, the surface of the metallic substrate can be treated by applying a coating, such as titanium nitride, iridium oxide, platinum, platinum iridium, and/or an electro-conductive polymer coating thereto. In still other aspects of the disclosure, the surface of the metallic substrate is both laser-textured and coated, with the treatments occurring in either order.

Also disclosed herein is a medical device including: a body; and at least one electrode disposed on the body, wherein the at least one electrode includes a metallic substrate. A surface of the substrate is modified in a manner that increases its effective surface area without inducing bulk heating and with a reduction in resistance of the metallic substrate when operating at a frequency within a cardiac medical range (e.g., less than about 20 kHz). For example, the surface of the substrate can be laser textured and/or coated.

The foregoing and other aspects, features, details, utilities, and advantages of the present invention will be apparent from reading the following description and claims, and from reviewing the accompanying drawings.

DETAILED DESCRIPTION

Figure 1:
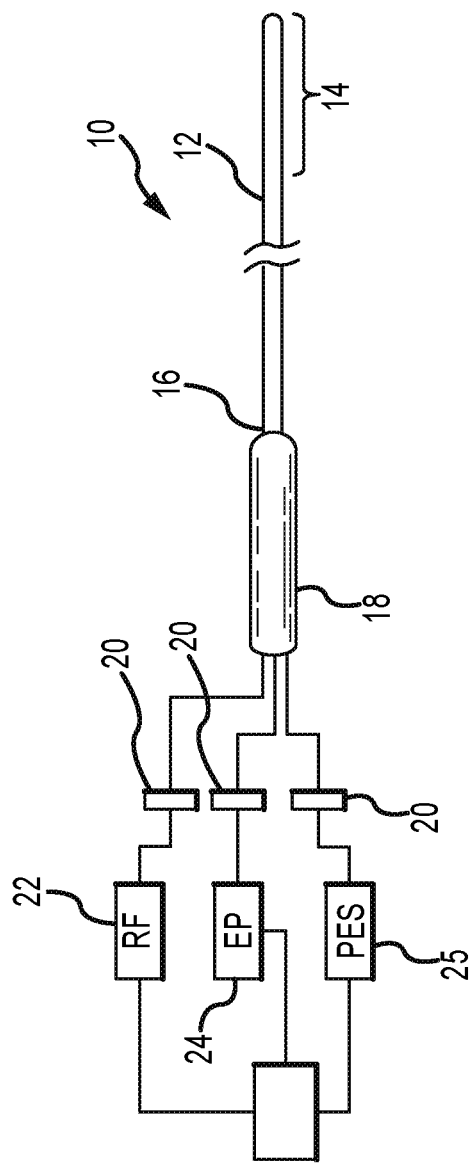
FIG. 1 schematically depicts an electrophysiology catheter and associated systems.

For purposes of illustration, the present teachings will be described in connection with a multi-electrode mapping and ablation catheter 10, such as illustrated in FIG. 1. As shown in FIG. 1, catheter 10 generally includes an elongate catheter body 12 having a distal region 14 and a proximal end 16. A handle 18 is shown coupled to proximal end 16. FIG. 1 also shows connectors 20. Connectors 20 are configured to be connected to a source of ablation energy (schematically illustrated as RF source 22, which can be, for example, the Ampere™ RF ablation generator of Abbott Laboratories, Abbott Park, Illinois), an electrophysiology mapping device or system (schematically illustrated as 24, which can be, for example, the EnSite Precision™ cardiac mapping system, also of Abbott Laboratories), and a programmable electrical stimulator (schematically illustrated as 25, which can be, for example the EP-4™ cardiac stimulator, also of Abbott Laboratories). Although FIG. 1 depicts three separate connectors 20, it is within the scope of the instant disclosure to have a combined connector 20 that is configured for connection to two or more of RF source 22, electrophysiology mapping device 24, and programmable electrical stimulator 25.

Various additional aspects of the construction of catheter 10 will be familiar to those of ordinary skill in the art. For example, the person of ordinary skill in the art will recognize that catheter 10 can be made steerable, for example by incorporating an actuator into handle 18 that is coupled to one or more steering wires that extend through elongate catheter body 12 and that terminate in one or more pull rings within distal region 14. Likewise, the ordinarily skilled artisan will appreciate that catheter 10 can be an irrigated catheter, such that it can also be coupled to a suitable supply of irrigation fluid and/or an irrigation pump. As a further example, those of ordinary skill in the art will appreciate that catheter 10 can be equipped with force feedback capabilities.

Insofar as such features are not necessary to an understanding of the instant disclosure, they are neither illustrated in the drawings nor explained in detail herein. By way of example only, however, catheter 10 can incorporate various aspects and features of the following catheters, all from Abbott Laboratories: the EnSite™ Array™ catheter; the FlexAbility™ ablation catheter; the Safire™ BLU™ ablation catheter; the Therapy™ Cool Path™ irrigated ablation catheter; the Livewire™ TC ablation catheter; and the TactiCath™ Quartz irrigated ablation catheter.

Figure 2:
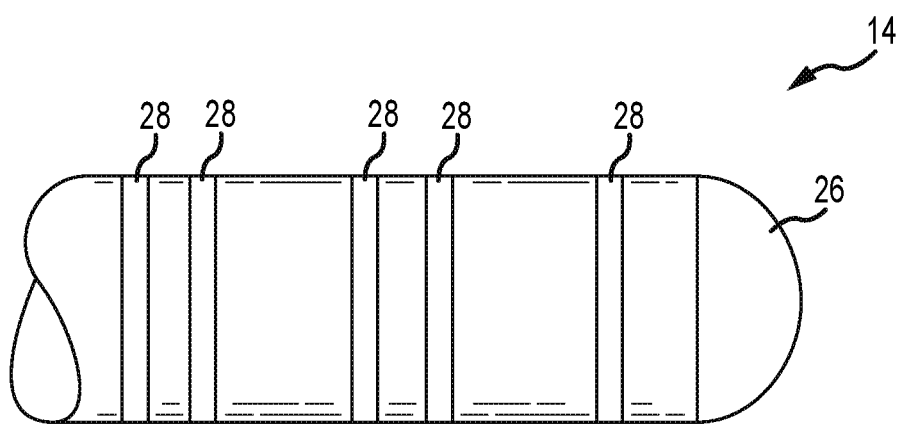
FIG. 2 is a close-up view of the distal region of the catheter shown in FIG. 1.

FIG. 2 is a close-up of distal region 14 of catheter 10. Distal region 14 of catheter 10 includes a tip electrode 26 positioned at its distal end and a plurality of additional electrodes 28 proximal of tip electrode 26. In particular, FIG. 2 depicts five ring electrodes 28. The person of ordinary skill in the art will understand and appreciate, however, that by varying the size (e.g., width) and spacing of electrodes 28, different diagnostic and/or therapeutic objectives and/or outcomes can be achieved. For example, the ordinarily skilled artisan will appreciate that, as electrodes 28 become smaller and closer together, the electrograms collected thereby will become sharper and more localized evidencing better depiction of local, near-field depolarization of the cardiac tissue in contact with the electrodes. Thus, it should be understood that distal region 14 can include any number of such electrodes 28 (e.g., 9 electrodes 28 for a decapolar catheter 10) and that the inter-electrode spacing can vary along the length of distal region 14.

Electrodes 28 may include any metal capable of detecting and conducting the local electrical signal. Suitable materials for electrodes 28 include, without limitation, platinum group metals (e.g., platinum, palladium, rhodium, osmium, ruthenium, iridium), alloys of platinum group metals (e.g., platinum-iridium alloys), and gold. In other embodiments of the disclosure, electrodes 28 include multiple layers of conductive materials, such as gold-coated copper.

Electrodes 28 can also be of various physical configurations. These include, by way of example only, ring electrodes, segmented ring electrodes, partial ring electrodes, flexible circuit electrodes, balloon electrodes, and spot electrodes. Various configurations of electrodes 28 (as well as electrode 26) are disclosed in International Publication No. WO 2016/182876, which is hereby incorporated by reference as though fully set forth herein.

Figure 3A:
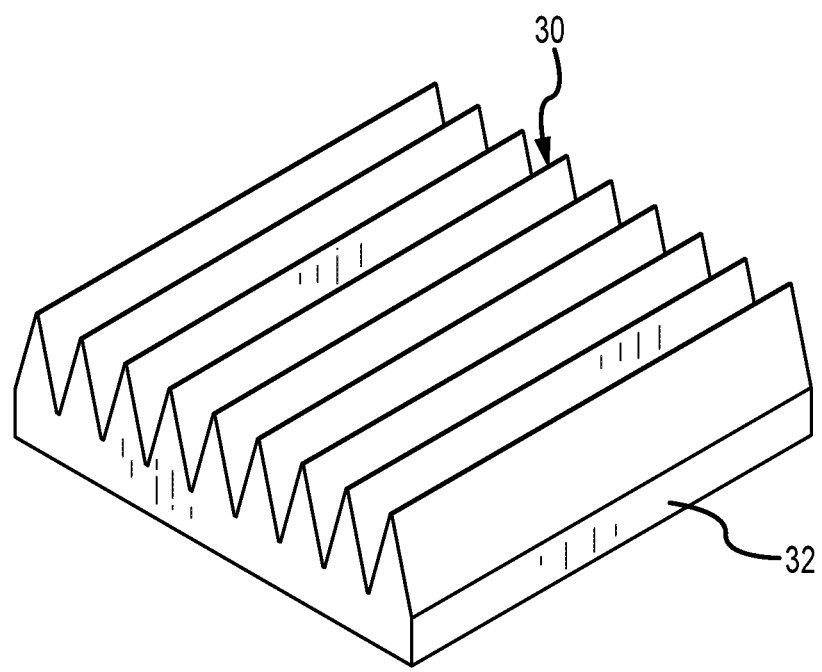
FIGS. 3A-3C are schematic illustrations of exemplary textured electrode surfaces according to aspects of the instant disclosure.
Figure 3B:
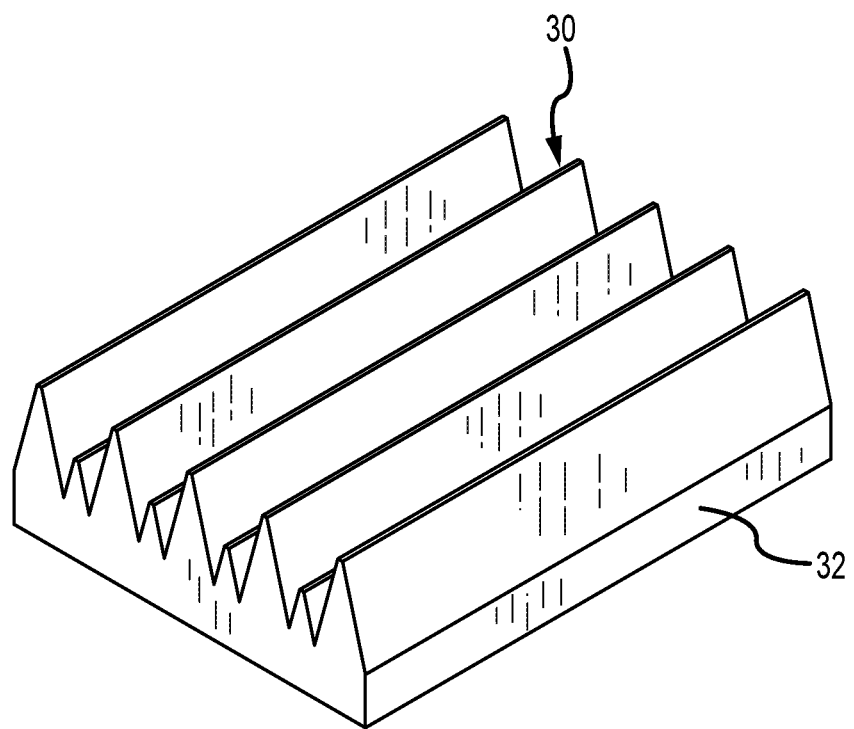
Figure 3C:
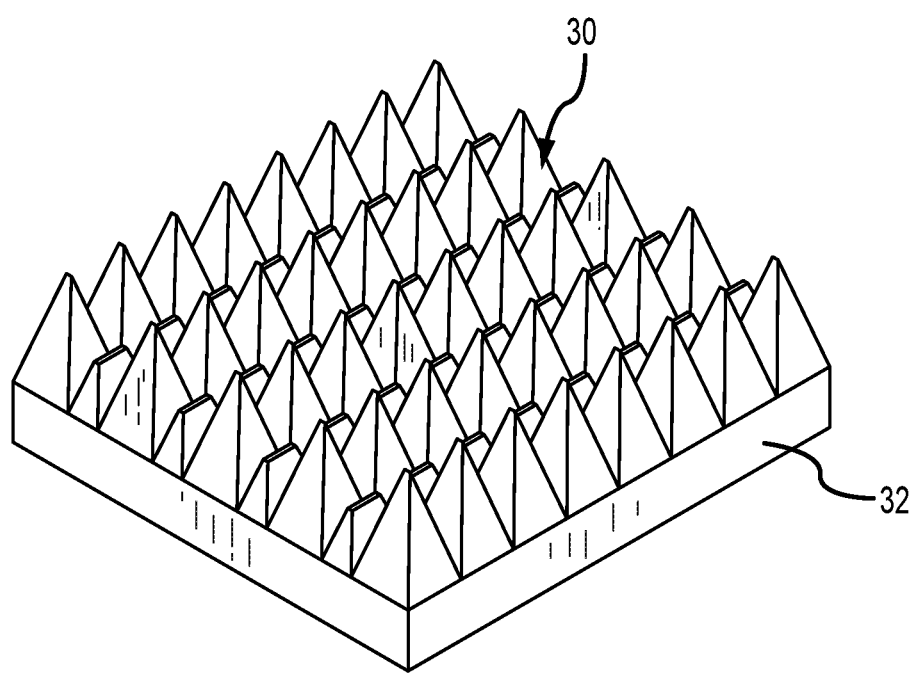

The instant disclosure provides electrodes having increased microscopic surface areas (that is, electrodes with surface areas exceeding those of planar electrodes having the same or similar dimensions). According to aspects of the disclosure, the increased microscopic surface area is achieved by treating a surface 30 of the electrode substrate 32 as shown in FIGS. 3A-3C. It is further desirable that the treatment increase the microscopic surface area of the electrode without causing bulk heating.

Electrodes having increased microscopic surface areas can be employed to good advantage in various electrophysiology devices including, without limitation, electrophysiology mapping catheters (e.g., basket catheters, HD grid catheters) and ablation catheters. The basic structure of such devices will be familiar to those of ordinary skill in the art, and are also illustrated in, inter alia, international application no. PCT/US2018/046953, United States patent application publication no. 2017/0112405, and U.S. Pat. No. 8,560,086, all of which are hereby incorporated by reference as though fully set forth herein. It should be understood, however, that the foregoing are merely representative of certain types of electrophysiology devices that can include electrodes according to the instant teachings; insofar as electrodes according to the instant disclosure can be employed to good advantage in other contexts, the foregoing list of electrophysiology devices should not be regarded as exclusive, exhaustive, or otherwise limiting.

In embodiments of the disclosure, surface 30 of electrode substrate 32 is treated by applying laser energy thereto, for example by using a femtosecond laser, to create a textured surface 30 on electrode substrate 32. FIGS. 3A through 3C illustrate three exemplary textured surfaces 30. The textured surface 30 of FIG. 3A has uniform peaks and valleys extending in a single dimension; the textured surface 30 of FIG. 3B has varying peaks and valleys extending in a single dimension; and the textured surface 30 of FIG. 3C has varying peaks and valleys extending in two dimensions. Of course, other patterns of textured surface 30 are contemplated and regarded as within the scope of the instant disclosure.

In general, the real component of the overall measured impedance (that is, the resistance) will have an interfacial component that is affected by the local ionic concentration, which results in a frequency dependency of the measured resistance. In aspects of the instant disclosure, therefore, it can be desirable for textured surface 30 to have a length scale comparable to the ionic double layer thickness (e.g., nanoscaled surfaces).

In other embodiments of the disclosure, surface 30 of electrode substrate 32 is treated by applying a coating thereto, such as a titanium nitride, iridium oxide, platinum, and platinum-iridium coatings. In other embodiments, the coating is a durable electro-conductive polymer coating, such as Amplicoat™ (Heraeus Medical Components LLC, Yardley, Pennsylvania). The coating may be applied to substrate 32 by physical vapor deposition, chemical vapor deposition, electrochemical deposition, or the like.

In still further embodiments of the disclosure, surface 30 of electrode substrate 32 is treated both by applying laser energy thereto and by applying a coating thereto. These treatments can be carried out in either order.

In general, the amount of impedance reduction relative to a planar electrode of the same or similar dimensions that results from the foregoing treatments can depend upon factors such as electrode dimensions, signal magnitude, signal frequency, and media ionic strength. As one example, at operating frequencies within the cardiac medical range (e.g., less than about 20 kHz), and measured relative to a planar electrode having a surface area of about 1 mm$^2$, treatments according to the instant teachings can yield impedance improvements (that is, reductions) of at least about 20%. It should also be understood that the percentage impedance improvement increases as the comparable planar electrode surface area decreases. Thus, in certain embodiments, the treatments disclosed herein can yield impedance improvements (that is, reductions) of at least about 30%, and, in some instances, of at least about 40%.

Although several embodiments have been described above with a certain degree of particularity, those skilled in the art could make numerous alterations to the disclosed embodiments without departing from the spirit or scope of this disclosure.

For example, the electrodes described herein can not only be formed prior to being attached to the body of a medical device (e.g., an electrophysiology catheter), but can also be formed following attachment to the body of the medical device.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of manufacturing a medical device, comprising:
   forming a medical device body;
   forming at least one electrode according to a process comprising:
      forming a metallic substrate;
      applying a coating to a surface of the metallic substrate; and
      treating the surface of the metallic substrate in a manner that increases a surface area of the metallic substrate and that reduces resistance of the metallic substrate when operating at a frequency within a cardiac medical range, wherein the treating step comprises creating a textured surface on the metallic substrate, and wherein the textured surface includes a plurality of peaks and valleys extending uniformly along at least one dimension; and
   securing the at least one electrode to the medical device body.

2. The method according to claim 1, wherein the treating step comprises laser etching the surface of the metallic substrate.

3. The method according to claim 1, wherein the coating comprises a metallic coating.

4. The method according to claim 3, wherein the metallic coating comprises at least one of titanium nitride, iridium oxide, platinum, and platinum-iridium.

5. The method according to claim 1, wherein the coating comprises an electrically-conductive polymer coating.

6. The method according to claim 1, wherein applying the coating to the surface of the metallic substrate comprises applying the coating to the surface of the metallic substrate via physical vapor deposition.

7. The method according to claim 1, wherein applying the coating to the surface of the metallic substrate comprises applying the coating to the surface of the metallic substrate via chemical vapor deposition.

8. The method according to claim 1, wherein applying the coating to the surface of the metallic substrate comprises applying the coating to the surface of the metallic substrate via electrochemical deposition.

9. A medical device, formed according to a process comprising:
   forming a medical device body;
   forming at least one electrode according to a process comprising:
      forming a metallic substrate;
      applying a coating to a surface of the metallic substrate; and
      treating the surface of the metallic substrate in a manner that increases a surface area of the metallic substrate and that reduces resistance of the metallic substrate when operating at a frequency within a cardiac medical range, wherein the treating step comprises creating a textured surface on the metallic substrate, and wherein the textured surface includes a plurality of peaks and valleys extending uniformly along at least one dimension; and
   securing the at least one electrode to the medical device body.

10. The medical device according to claim 9, wherein the treating step comprises laser etching the surface of the metallic substrate.

11. The medical device according to claim 9, wherein the coating comprises a metallic coating.

12. The medical device according to claim 11, wherein the metallic coating comprises at least one of titanium nitride, iridium oxide, platinum, and platinum-iridium.

13. The medical device according to claim 9, wherein the coating comprises an electrically-conductive polymer coating.

14. The medical device according to claim 9, wherein applying the coating to the surface of the metallic substrate comprises applying the coating to the surface of the metallic substrate via physical vapor deposition.

15. The medical device according to claim 9, wherein applying the coating to the surface of the metallic substrate comprises applying the coating to the surface of the metallic substrate via chemical vapor deposition.

16. The medical device according to claim 9, wherein applying the coating to the surface of the metallic substrate comprises applying the coating to the surface of the metallic substrate via electrochemical deposition.

17. A medical device comprising:
a medical device body;
at least one electrode secured to the medical device body, the at least one electrode comprising:
- a metallic substrate having a surface, wherein the surface includes a surface treatment that increases a surface area of the metallic substrate and that reduces resistance of the metallic substrate when operating at a frequency within a cardiac medical range, wherein the surface treatment comprises a textured surface including a plurality of peaks and valleys extending uniformly along at least one dimension; and
- a coating applied to the surface of the metallic substrate.

18. The medical device according to claim 17, wherein the surface treatment comprises a laser-etched pattern.

19. The medical device according to claim 17, wherein the coating comprises a metallic coating.

20. The medical device according to claim 19, wherein the metallic coating comprises at least one of titanium nitride, iridium oxide, platinum, and platinum-iridium.

21. The medical device according to claim 17, wherein the coating comprises an electrically-conductive polymer coating.

* * * * *